United States Patent [19]

Kohayakawa et al.

[11] Patent Number: 4,717,952
[45] Date of Patent: Jan. 5, 1988

[54] MEDICAL TELEVISION SYSTEM

[75] Inventors: Yoshimi Kohayakawa; Kazunobu Kobayashi, both of Yokohama; Shinya Tanaka, Tokyo; Haruhisa Madate, Kawasaki; Takeshi Kitamura, Tokyo, all of Japan

[73] Assignee: Canon Kabushiki Kaisha, Tokyo, Japan

[21] Appl. No.: 871,291

[22] Filed: Jun. 6, 1986

[30] Foreign Application Priority Data

Jun. 14, 1985 [JP] Japan .................................. 60-129401
Oct. 18, 1985 [JP] Japan .................................. 60-232801
Oct. 18, 1985 [JP] Japan .................................. 60-232803

[51] Int. Cl.$^4$ .......................... H04N 7/18; H04N 5/33
[52] U.S. Cl. ..................................... 358/113; 128/633; 128/634; 351/206; 358/50; 358/98; 358/108; 358/209
[58] Field of Search ................ 358/113, 209, 108, 93, 358/50, 98, 44, 211; 128/633, 634; 351/206, 207, 208

[56] References Cited

U.S. PATENT DOCUMENTS

| 3,533,683 | 10/1970 | Stark | 351/206 |
|---|---|---|---|
| 4,016,597 | 4/1977 | Dillon | 358/211 |
| 4,123,777 | 10/1978 | Sekiguchi | 358/50 |
| 4,213,462 | 7/1980 | Sato | 128/634 |
| 4,266,861 | 5/1981 | Sawa | 351/208 |
| 4,305,398 | 12/1981 | Sawa | 128/633 |
| 4,437,111 | 3/1984 | Inai | 358/209 |
| 4,468,104 | 8/1984 | Nunokawa | 351/206 |
| 4,469,416 | 9/1984 | Isono | 351/206 |
| 4,620,318 | 10/1986 | Hill | 351/208 |
| 4,631,580 | 12/1986 | Taube | 351/206 |

OTHER PUBLICATIONS

*Optical Spectra*, Sep. 1970, p. 29, "A See-in-the-Dark Tube for Commercial Application".

Primary Examiner—Howard W. Britton
Attorney, Agent, or Firm—Fitzpatrick, Cella, Harper & Scinto

[57] ABSTRACT

A medical television system includes a television camera and a selector. The television camera includes a filter for separating visible light into three wavelength regions and transmitting near-infrared rays, and an image pickup element having sensitivity to both visible light and near-infrared rays. The selector selectively supplies the visible light separated into the three wavelength components or the near-infrared rays to the television camera.

9 Claims, 19 Drawing Figures

MEDICAL TELEVISION SYSTEM

BACKGROUND OF THE INVENTION

1. Field of the Invention

The present invention relates to a medical television system for producing color and near-infrared images with a single television camera.

2. Related Background Art

A conventional television camera does not have sensitivity in the near-infrared region in order to guarantee color reproduction. In order to produce both near-infrared and color images, a separate camera having sensitivity for the near-infrared region must be prepared. For this reason, the total system results in high cost and is bulky and complicated.

Figure 1:
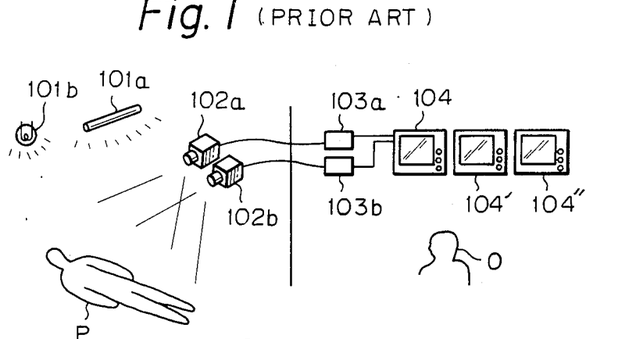
FIGS. 1, 2, 3 and 4 are schematic views for explaining conventional apparatuses.

For example, in an intensive care system of FIG. 1, a sickroom is illuminated by an illumination light source 101a of visible light during the day to allow an operator (e.g., a nurse) to monitor a patient P through a color television camera 102a, a control unit 103a, and a color monitor 104. At night, the sickroom is illuminated with a nighttime illumination light source 101b for emitting near-infrared light so as not to interfere with the patients sleep. The patient P is then monitored through a near-infrared television camera 102b, a control unit 103b, and a color monitor 104. Other monitors 104' and 104" are also arranged in the monitor room to allow simultaneous monitoring of patients in other sickrooms. Such a 24-hour intensive care system is used particularly for monitoring patients in critical condition. Therefore, the color television camera 102a, the near-infrared television camera 102b, and their respective control units 103a and 103b must be installed in each sickroom, resulting in high cost.

Japanese Patent Application Disclosure No. 183830/1982 and the like describe apparatuses for projecting a still image of an eye fundus from a nonmydriatic-type fundus camera as a television image. In these conventional apparatuses, a fundus image recorded on a conventional silver chloride film is also displayed on a television monitor to check if the film image is properly photographed.

Figure 2:
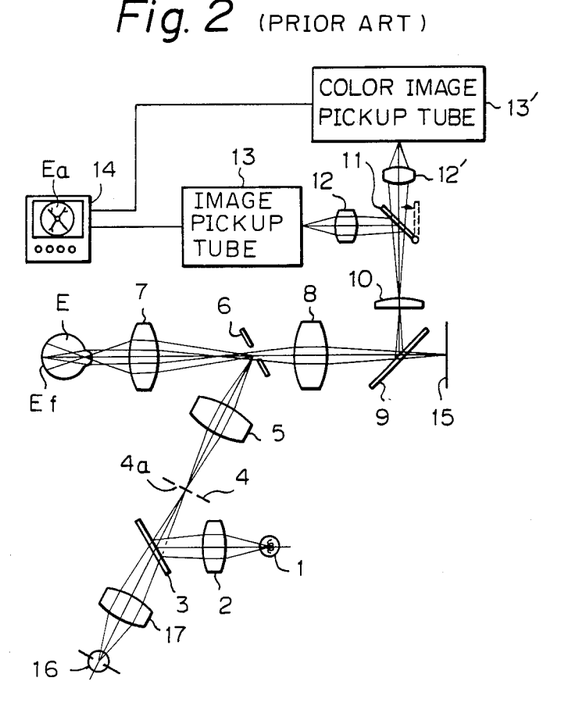
Figure 3:
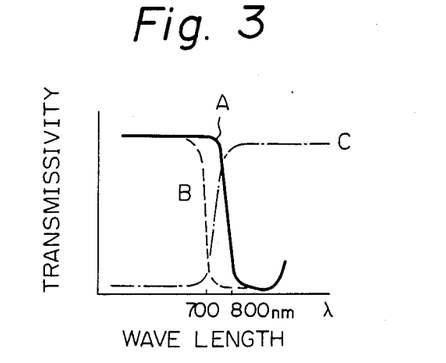

An example of this type of conventional apparatus is described with reference to FIG. 2. Light from an observation light source 1 of a tungsten lamp or the like illuminates a ring-like opening 4a of a ring slit 4 through a condenser lens 2 and a dichroic mirror 3. As shown in FIG. 3, the dichroic mirror 3 transmits visible light and reflects infrared rays, as indicated by a characteristic curve A. Light through the ring-like opening 4a is temporarily focused near an apertured mirror 6 by a relay lens 5, is focused again near the cornea of an eye E by an objective lens 7 arranged between the apertured mirror 6 and the eye E, and illuminates the eye fundus Ef. Light reflected by the fundus Ef is temporarily focused by the objective lens 7, passes through an aperture of the apertured mirror 6, and is focused near a field lens 10 through a photographing lens 8 and a dichroic mirror 9. The light is then further focused on a light-receiving surface of an image pickup tube 13 through a reflecting mirror 11 and a relay lens 12. The dichroic mirror 9 also has the characteristics given by the curve A in FIG. 3. The fundus image guided to the image pickup tube 13 is displayed as a fundus image Ea on the CRT of a television monitor 14. A film 15 is arranged behind the dichroic mirror 9 through a shutter (not shown). A condenser lens 17 and a photographing light source 16 of a strobe tube are arranged behind the dichroic mirror 3.

The photographing light source 16 is operated during photographing. Visible light from the light source 16 illuminates the ring-like opening 4a of the ring slit 4 through the dichroic mirror 3, and then illuminates the fundus Ef of the eye E through the relay lens 5, the apertured mirror 6, and the objective lens 7. Light reflected by the fundus Ef passes through the objective lens 7 and the apertured mirror 6 and is focused and recorded on the film 15 through the photographing lens 8 and the dichroic mirror 9.

Figure 4:
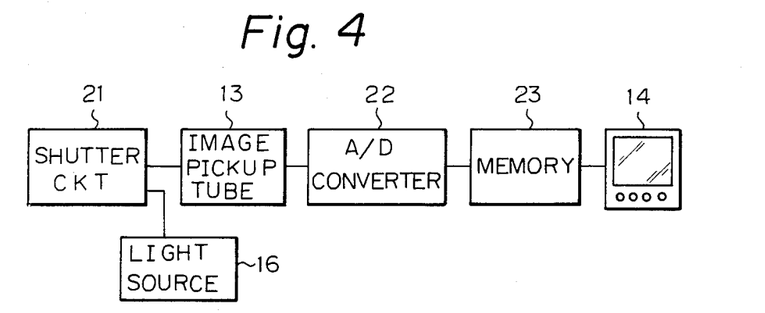

The photographing light source 16 is operated upon operation of the shutter. At the same time, a circuit for producing a still image, as shown in FIG. 4, is operated in response to the shutter signal. The signal from a shutter circuit 21 causes the photographing light source 16 to operate and at the same time is supplied to the image pickup tube 13. An output from the image pickup tube 13 is supplied to an A/D converter 22. The digital signal from the A/D converter 22 is stored in a frame memory 23. The stored data is input to the television monitor 14. The fundus image Ea as the photographed image is monitored on the television monitor 14 so that the photographed image can be checked on the monitor 14. In doing so, the operator can immediately judge whether the image on the film 15 is properly photographed. If it is judged that this is not the case, a necessary countermeasure can be taken immediately. For example, the fundus image can be photographed again.

In the system described above, as is apparent from the characteristics of the dichroic mirrors 3 and 9, since the image pickup tube 13 and the television monitor 14 are, respectively, a monochromatic tube and a monochromatic monitor which have sensitivity to near-infrared rays, a monochromatic still image can be obtained. However, a color still image of the fundus Ef cannot be produced. Another conventional system of this type is known in which flare states on the photographed image are precisely detected so as to allow judgement on whether the image on the film 15 is accurate. According to this system, the dichroic mirror 9 is replaced with a half mirror, the reflecting mirror 11 is set to be movable, as shown in FIG. 2, and a relay lens 12' and an image pickup tube 13' having sensitivity to visible light are arranged behind the reflecting mirror 11. A fundus still image of visible light can be produced by the image pickup tube 13'. In the above system, if the image pickup tube 13' and the television monitor 14 are replaced with a color image pickup tube and a color television monitor, respectively, a color fundus still image can be obtained. However, the system must have two types of image pickup tubes 13 and 13'. The system mechanism therefore becomes complicated and bulky.

SUMMARY OF THE INVENTION

It is an object of the present invention to provide a medical television system for integrating two different types of television camera systems to provide equivalent functions with a simpler mechanism.

It is another object of the present invention to provide a fundus camera of both mydriatic and nonmydriatic type, wherein a color image can be observed through a television camera when a mydriatic is used and a monochromatic image can be observed through the same television camera when a mydriatic is not used and, at the same time, a fundus image recorded on conventional silver chloride film can be recorded as an electronic image.

BRIEF DESCRIPTION OF THE DRAWINGS

FIGS. 5 to 8 show embodiments of medical television systems according to the present invention, in which FIGS. 9 to 15 show an embodiment exemplifying a fundus camera system, in which

DESCRIPTION OF THE PREFERRED EMBODIMENTS

Figure 5:
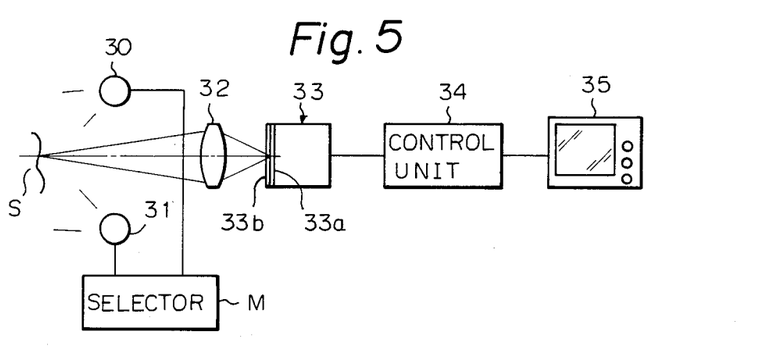
FIG. 5 shows a system configuration.

FIG. 5 shows a system configuration of a first embodiment. The system includes a daytime illumination light source 30 and a nighttime illumination light source 31 for an object S to be detected. One of the light sources 30 and 31 is disabled by a selector M. An objective lens 32 is arranged opposite the object S. A color television camera 33 is arranged behind the objective lens 32. An output from the color television camera 33 is supplied to a color monitor 35 through a control unit 34. The color television camera 33 comprises a single image pickup tube consisting of a single image pickup element 33a having sensitivity to visible light and near-infrared rays, and a mosaic three-color stripe filter 33b arranged in front of the image pickup element 33a. A three-channel signal can be obtained through the filter 33b.

Figure 6A:
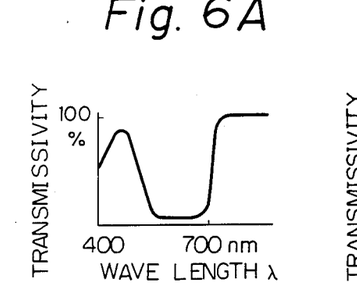
FIG. 6A, 6B, and 6C show characteristics of a three-color stripe filter, FIG. 7 are graphs for a light source and the filter.
Figure 6B:
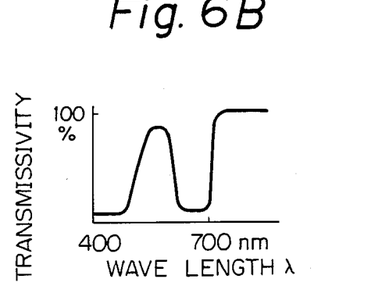
Figure 6C:
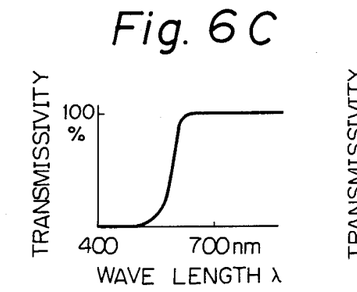

The characteristics of the three-color stripe filter 33b are given as spectral characteristics in FIGS. 6A, 6B and 6C. The three filter components selectively transmit visible light therethrough and transmit all near-infrared rays having a wavelength of 700 nm or more. Visible light or near-infrared rays are incident on the color television 33 having this arrangement through the objective lens 32. If only visible light is incident on the television camera 33, a color image of the object S can be obtained. However, if only near-infrared rays are incident, a near-infrared image is obtained.

If the television camera 33 is used in the intensive care system described above, the two television cameras 102a and 102b can be replaced with the television camera 33. More specifically, if the daytime illumination light source 30 has light-emission characteristics represented by a curve B in FIG. 7 and the nighttime illumination light source 31 has light-emission characteristics represented by a curve A in FIG. 7, the previously described effect can be obtained simply by switching the light sources 30 and 31. The normal daytime light source 30 comprises sun rays or a fluorescent lamp. Such a light source also includes near-infrared rays. In this case, an infrared-ray blocking filter is inserted in front of the television camera 33.

In the conventional apparatus described above, near-infrared rays are used in order to prevent interference with the patient's sleep at night. However, near-infrared rays can also be used in a more positive way. For example, it is known that near-infrared rays are transmitted deeper into the skin of a living organism than visible light. By utilizing this phenomenon, useful information can be acquired through irradiating the organism with near-infrared rays.

Figure 8:
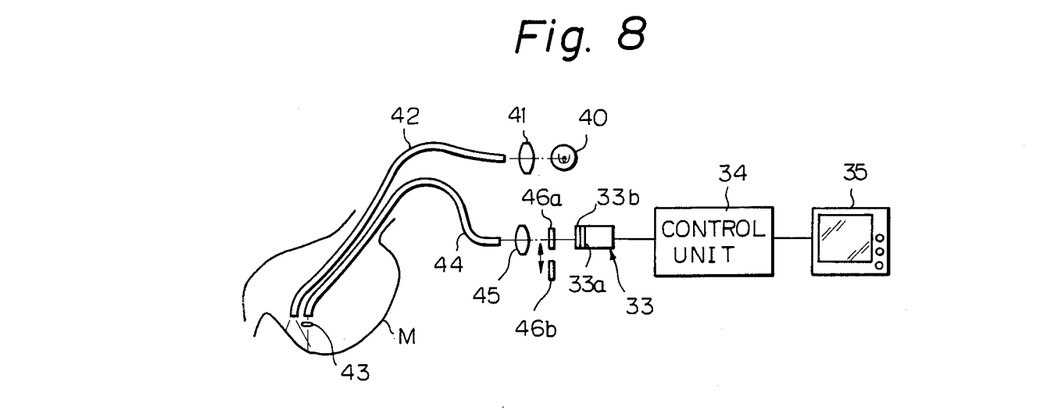
FIG. 8 shows a system configuration of another embodiment of the present invention.

FIG. 8 shows an application for obtaining such information. More specifically, a television camera type endoscope is exemplified as an apparatus for observing the digestive system. Light from a light source 40 for generating visible light and near-infrared rays illuminates an inner wall M of a patient's stomach through a condenser lens 41 and a light guide 42. An image of the inner wall M of the stomach is focused on an image pickup surface of the color television 33 through a lens 43, a light guide 44, and a focusing lens 45. The image can be observed on the color television monitor 35 through the control unit 34.

Figure 7:
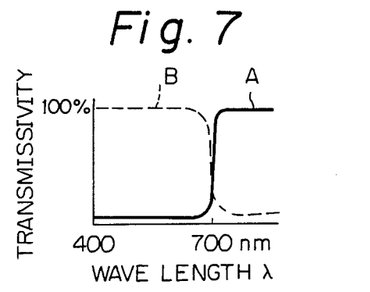

With this arrangement, filters 46a and 46b having the characteristics represented by curves A and B in FIG. 7 are replaced in front of the television camera 33. As a result, both a near-infrared or a color image of the inner wall M of the stomach can be monitored on the color television monitor 35. Since a conventional endoscope having both the above functions would be increased in size, sophisticated manipulation thereof would cause increased physical discomfort and pain to the patient. Therefore, the application described above is very useful in this medical field.

In the television camera endoscope, if the light sources are switched from visible light to near-infrared rays and vice versa, switching between the filters 46a and 46b is not required.

In the above embodiment, a single tube color camera is used as the color television camera 33. However, a three-tube color television camera may also be used. In this case, the stripe filter 33b does not comprise a mosaic filter, but filters having the characteristics shown in FIGS. 6A, 6B and 6C are respectively arranged for the channel image pickup tubes. However, if higher sensitivity or resolution is not required, the single tube color camera is preferred to constitute an inexpensive system. The means for selecting the rays incident on the television camera 33 are exemplified by the light sources and filters, which are independent from the illumination system and the camera. However, these may be combined according to the characteristics of the light sources and the properties of the object to be illuminated.

Another embodiment will be described wherein the present invention is applied to a fundus camera.

Figure 9:
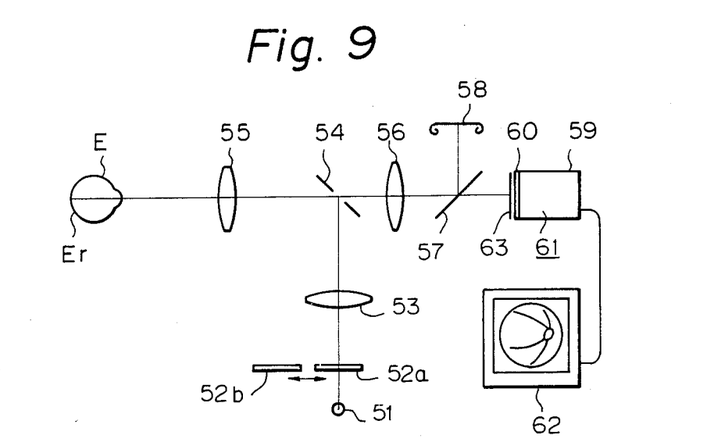
FIGS. 9 and 10 are system configurations for selecting visible light and near-infrared rays in an illumination optical system.

FIG. 9 shows an embodiment of a fundus camera. A light source is a source (e.g., an incandescent lamp 51) for emitting visible light and near-infrared rays. In the recording mode, a strobe tube can be used together with the incandescent lamp. Light from the incandescent lamp 51 passed through a filter 52a (or 52b), a lens 53, an apertured mirror 54, and a lens 55. The light then illuminates a fundus Er of an eye E to be examined. Light reflected by the fundus Er is focused on a film 58 or an image pickup element 60 in a color television camera 59, through a lens 55, the aperture mirror 54, a lens 56, and a selection mirror 57.

The color television camera 59 has the image pickup element 60 having sensitivity for visible light and near-infrared rays, and a video generator 61. A video signal is supplied to a color monitor 62 to monitor a fundus image. In this embodiment, the color television camera 59 comprises a single tube camera. A mosaic three-color stripe filter 63 having the characteristics shown in FIGS. 6A, 6B and 6C is inserted in front of the image pickup element 60 to obtain a three-channel signal.

The color components of the stripe filter 63 are red, green, and blue. However, a combination of complementary colors of red, green and blue can also be utilized.

Of the filters 52a and 52b alternately inserted in the illumination optical system, the filter 52a is a near-infrared ray transmission filter whose characteristics are given by the curve A in FIG. 7. The filter 52b is a visible light transmission filter whose characteristics are given by the curve B in FIG. 7. If a mydriatic is not used, the filter 52a is inserted. Otherwise, the filter 52b is inserted. Therefore, the fundus image can be obtained as a monochromatic or color image, and can be effectively utilized for alignment.

In the above embodiment, the color television camera 59 is a single tube color camera, but can be a three-tube color camera. In this case, the filter 63 is not a mosaic filter, but filters of the characteristics shown in FIGS. 6A, 6B and 6C are arranged for the three channels.

Figure 10:
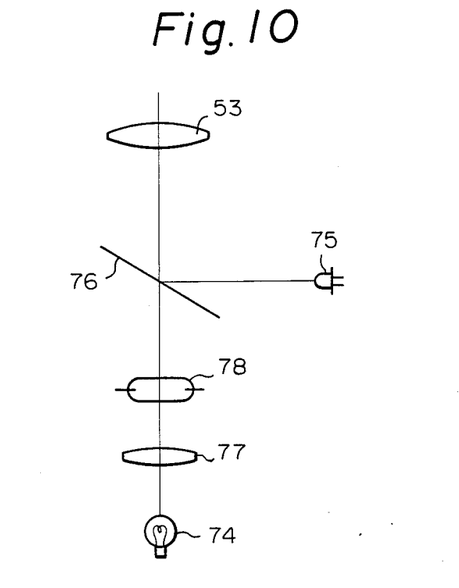

FIG. 10 shows still another embodiment of the present invention. An incandescent lamp 74 and an infrared light-emitting diode 75 are used in place of the filters 52a and 52b, and are alternately switched. A dichroic mirror 76 is arranged in the illumination system optical path to reflect near-infrared rays from the infrared LED 75 and transmit visible light from the incandescent lamp 74. The incandescent lamp 74 and the infrared LED 75 are selectively used in accordance with the mydriatic or nonmydriatic type. A condenser lens 77 and a film photographing strobe 78 are inserted between the incandescent lamp 74 and the dichroic mirror 76. In this embodiment, no movable mechanism is employed to switch between the filters 52a and 52b. Thus, the entire system configuration can be simplified.

Figure 11:
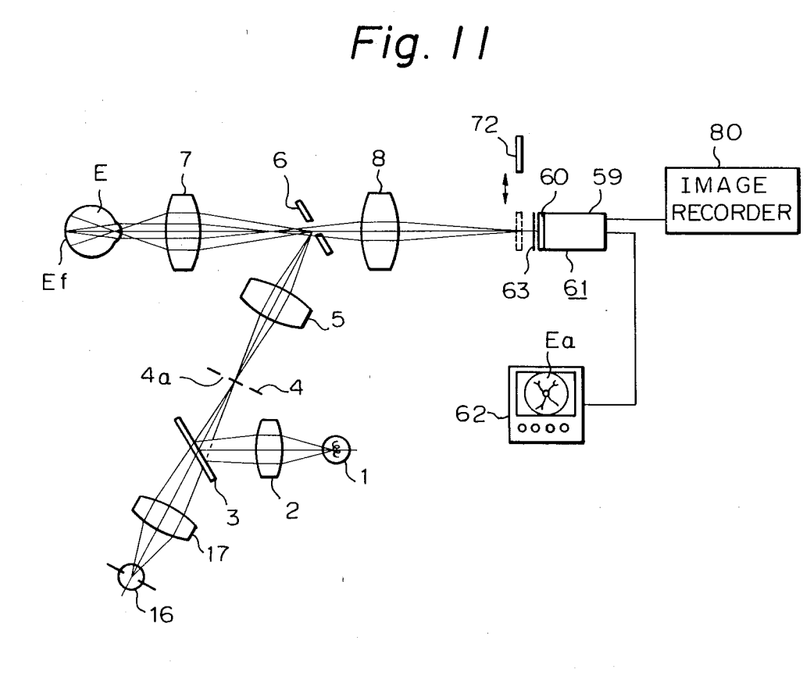
FIG. 11 shows a system configuration of another embodiment for selecting visible light and near-infrared rays within an illumination optical system.

Still another embodiment of a fundus camera is shown in FIG. 11. The same reference numerals as in FIG. 2 denote the same parts in FIG. 11, and a detailed description thereof will be omitted.

In the embodiment of FIG. 11, the imaging surface of a single color television camera 59 is aligned with a position corresponding to the conventional film 15. A detachable filter 72 is arranged in the optical path in front of the color television camera 59. An image recording unit 80 for recording a one-frame image signal is connected to the color television camera 59. The image recording unit 80 may be one of the recently developed still video camera recording units, i.e., a unit for recording an image on a still video floppy disk, or an optical card recording unit.

In the observation mode, the filter 72 is removed from the optical path. When an observation light source 1 is turned on, a fundus Ef of an eye E to be examined is illuminated with near-infrared rays. Light reflected by the fundus Ef is guided onto the imaging surface of the color television camera 59. A fundus image Ea derived from the near-infrared rays can be displayed on the monitor 62.

In the photographing mode, visible light from a photographing light source 16 is reflected by the fundus Ef. Similarly, light is guided onto the imaging surface of the color television camera 59. In this case, the filter 72 is inserted in the optical path in synchronism with operation of the photographing light source 16. The near-infrared rays always emitted from the observation light source 1 are cut off by the filter 72, and the color television camera 59 produces a good color signal representing a clear image of the fundus Ef. If an output from the color television camera 59 is sent to the image recording unit 80 in synchronism with the operation of the photographing light source 16, a fundus color still image can be recorded with a relatively simple arrangement.

Figure 12:
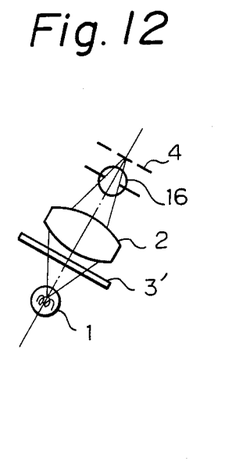
FIGS. 12 and 13 show system configurations of an illumination system of still other embodiments.
Figure 13:
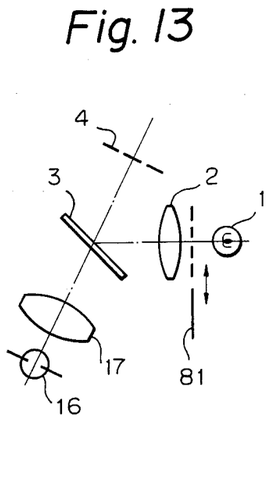

Coupling between the observation light source 1 and the photographing light source 16 in FIG. 11 can be replaced with that shown in FIG. 12. The characteristics of a filter 3' used in place of the dichroic mirror 3 are given by a curve C in FIG. 3. In this case, even if light from the photographing light source 16 includes near-infrared rays, they can be cut off by the filter 72.

Provision of the filter 72 is essentially equivalent to that of a shutter 81 in front of the observation light source 1. Only the visible light component is extracted by the dichroic mirror 16 from light emitted from the photographing light source 16. Light from the observation light source 1, which is continuously operated, is shielded by the shutter 81. Therefore, the light component incident on the color television camera 59 is only the visible light component.

If the image signal reception timing of the image recording device 80 is an arbitrary one asynchronous with operation of the photographing light source 16, a still image of the eye E to be examined can be recorded with the near-infrared components. With this additional function, in order to eliminate recorded image flow (i.e., blurring) due to small vibrations of the eye E, a visible light blocking/near-infrared transmission filter can be inserted in front of the photographing light source 16 in FIG. 12. In this manner, the near-infrared rays from short-time radiation from the photographing light source 16 can be utilized. In this case, the filter 72 in FIG. 11 should not be inserted in the optical axis.

Figure 14:
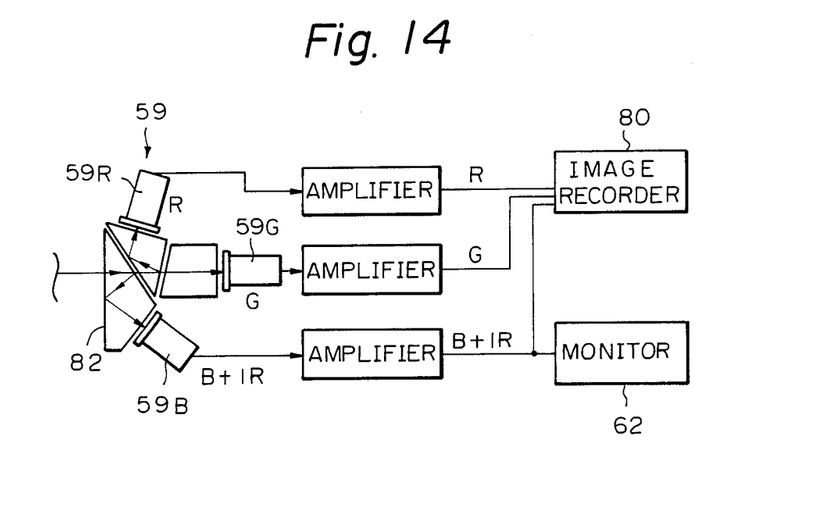
FIG. 14 shows a system configuration of an image pickup system in still another embodiment.
Figure 15A:
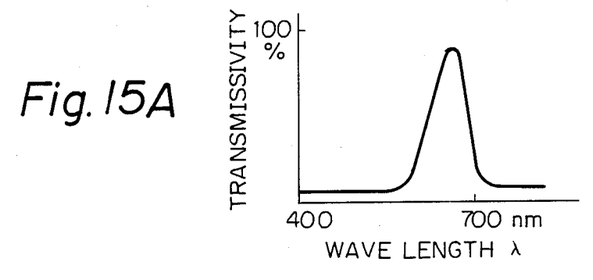
FIGS. 15A, 15B and 15C are graphs showing characteristics of a spectral prism.
Figure 15B:
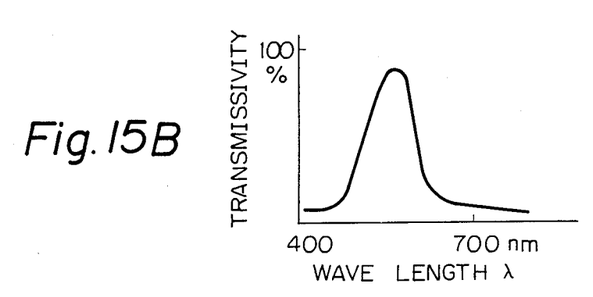
Figure 15C:
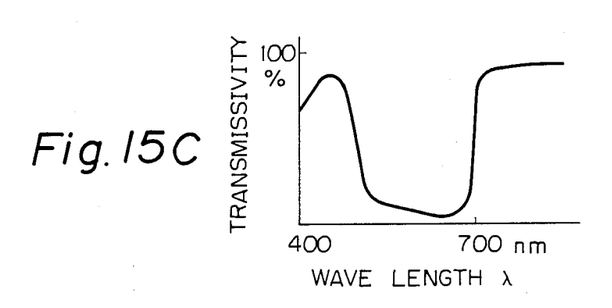

In the embodiment of FIG. 11, the single tube color television camera 59 is used. However, if the resolution of the image recording unit 80 is appropriately compensated, a three-tube color television camera can be effectively used to obtain a better image. Such an arrangement is illustrated in FIG. 14. A spectral prism 82 is arranged in front of image pickup tubes 59R, 59G and 59B. The characteristics of the spectral prism 82 are shown in FIGS. 15A, 15B and 15C. Light components incident on the respective image pickup tubes are sent to the image recording unit through amplifiers. In this case, if the image pickup tube 59B has sensitivity to near-infrared rays IR, a monitor 62 can be operated for near-infrared rays. In addition, the light rays can be split into three portions instead of using the spectral prism 82. In this case, the filters having the corresponding characteristics shown in FIG. 6 can be arranged for the respective channels.

What is claimed is:
1. A medical television system, comprising:
    an illumination optical system for illuminating an object to be examined;
    a focusing optical system for focusing an image of said object on a predetermined plane;
    a filter located between said object and said predetermined plane for separating visible light into three wavelength regions and transmitting near-infrared rays;

an image pickup element located on said predetermined plane and having sensitivity to both visible light and near-infrared rays;

selecting means for selectively supplying the visible light or the near-infrared rays, which are reflected by said object, to said image pickup element; and a television monitor connected to said pickup element to indicate a visible light image or a near-infrared ray image.

2. A system according to claim 1, wherein said system comprises both a visible light source and a near-infrared source, both of which illuminate an object to be examined, said selecting means includes means for disabling one of said visible light source and said near-infrared source.

3. A system according to claim 1, wherein said illumination optical system comprises a light source which emits visible lights and near-infrared rays simultaneously and said selecting means comprises a filter selectively inserted between the object and said light source.

4. A system according to claim 1, wherein said illumination optical system comprises a light source which emits visible light and near-infrared rays simultaneously and said selecting means comprises a filter inserted between the object and said image pickup element.

5. A system according to claim 1, wherein said image pickup element is of a single tube type, and said filter comprises a three-color stripe filter.

6. A system according to claim 1, wherein said image pickup element is of a three-tube type, and the near-infrared rays enter at least one part of said image pickup element.

7. An ophthalmologic system including a medical television apparatus, comprising:

an illumination optical system for illuminating a fundus of an eye to be examined;

a focusing optical system for focusing a fundus image on a predetermined plane;

a television camera including a filter for separating visible light into three wavelength regions and transmitting near-infrared rays, and including an image pickup element located on the predetermined plane and having sensitivity to both visible light and near-infrared rays; and selecting means for selectively supplying the visible light or the near-infrared rays, which are reflected by the fundus, to said television camera.

8. An ophthalmologic system including a medical television apparatus, comprising:

an illumination optical system for illuminating a fundus of an eye to be examined;

a focusing optical system for focusing a fundus image on a predetermined plane;

a television camera including a filter for separating visible light into three wavelength regions and transmitting near-infrared rays, and including an image pickup element located on the predetermined plane and having sensitivity to both visible light and near-infrared rays;

selecting means for selectively supplying the visible light or the near-infrared rays, which are reflected by the fundus, to said television camera; and an image recording unit for recording a one-frame image signal from said television camera.

9. A television system comprising:

an illumination optical system for illuminating an object;

a focusing optical system for focusing an image of said object on a predetermined plane;

a filter located between said object and said predetermined plane for separating visible light into three wavelength regions and transmitting near-infrared rays;

an image pickup element located on said predetermined plane and having sensitivity to both visible light and near-infrared rays;

selecting means for selectively supplying the visible light or the near-infrared rays, which are reflected by said object, to said image pickup element; and a television monitor connected to said pickup element to indicate a visible light image or a near-infrared ray image.

* * * * *